United States Patent
Schueler et al.

(10) Patent No.: US 10,031,054 B2
(45) Date of Patent: Jul. 24, 2018

(54) SOLID-PHASE MICROEXTRACTION

(71) Applicant: CTC Analytics AG, Zwingen (CH)

(72) Inventors: Kai Heinrich Schueler, Hoffeld (CH); Melchior Zumbach, Lenzburg (CH)

(73) Assignee: CTC ANALYTICS AG, Zwingen (CH)

( * ) Notice: Subject to any disclaimer, the term of this patent is extended or adjusted under 35 U.S.C. 154(b) by 980 days.

(21) Appl. No.: 13/953,389

(22) Filed: Jul. 29, 2013

(65) Prior Publication Data

US 2014/0030818 A1   Jan. 30, 2014

(30) Foreign Application Priority Data

Jul. 30, 2012   (EP) .................................... 12405074

(51) Int. Cl.
*B01L 9/06* (2006.01)
*G01N 1/40* (2006.01)
*G01N 1/22* (2006.01)

(52) U.S. Cl.
CPC .......... *G01N 1/405* (2013.01); *G01N 1/2214* (2013.01); *Y10T 436/255* (2015.01)

(58) Field of Classification Search
CPC ......... G01N 35/0098; G01N 2030/025; G01N 7/04; G01N 2035/023; B01L 90/06; B01L 19/0046
USPC ............... 422/527, 560, 69, 68.1, 70, 89, 88
See application file for complete search history.

(56) References Cited

U.S. PATENT DOCUMENTS

| | | |
|---|---|---|
| 5,693,228 A | 12/1997 | Koehler et al. |
| 2003/0021733 A1 | 1/2003 | Andresen et al. |
| 2005/0011831 A1* | 1/2005 | Pawliszyn ................ G01N 1/40 210/634 |
| 2007/0248500 A1* | 10/2007 | Pawliszyn .......... B01J 20/28014 422/400 |
| 2009/0199621 A1 | 8/2009 | Land, III |
| 2009/0260456 A1* | 10/2009 | Degli Esposti ........ G01N 1/405 73/863.21 |
| 2010/0295557 A1 | 11/2010 | Probst et al. |
| 2010/0313688 A1 | 12/2010 | Hiltbrand |

FOREIGN PATENT DOCUMENTS

| | | |
|---|---|---|
| DE | 10 2009 022 314 A1 | 11/2010 |
| EP | 0 794 822 B1 | 8/2001 |
| EP | 2 261 676 A1 | 12/2010 |
| WO | WO 91/15745 A1 | 10/1991 |
| WO | WO 2007/032039 A2 | 3/2007 |

OTHER PUBLICATIONS

Varian, "8200 CX AutoSampler Operator's Manual," 1995.

* cited by examiner

*Primary Examiner* — Christine T Mui
(74) *Attorney, Agent, or Firm* — Birch, Stewart, Kolasch & Birch, LLP

(57) ABSTRACT

In a method for performing a solid-phase micro-extraction, a holding device connected to an extraction device and secured on an adapter is held, while an actuating device connected to a guide device is moved. A device for performing a solid-phase microextraction comprises an actuating device connected to a guide device, and a holding device connected to an extraction device, wherein the extraction device is guided at least partially in the guide device, and wherein the extraction device is movable relative to the guide device by means of an actuation of the actuating device.

11 Claims, 2 Drawing Sheets

SOLID-PHASE MICROEXTRACTION

TECHNICAL FIELD

The invention relates to a method for performing a solid-phase microextraction, to a corresponding device for performing a solid-phase microextraction, and to an adapter for receiving a device for performing a solid-phase microextraction and for mounting on a tool holder.

PRIOR ART

Solid-phase microextraction (SPME) has been known since the beginning of the 1990s. The central part of the SPME device is typically a fiber. The latter can be present in different forms, with the polarity in particular being varied. Depending on the polarity of the fiber material, an analyte with substantially the same polarity can be extracted in the method from a matrix, which can be both gaseous and also liquid. The analyte of the matrix thus accumulates on the fiber, whereupon the analyte on the fiber can be desorbed, for example in a gas chromatograph, and analyzed.

WO 91/15745 A1 (Supelco) relates to a device and a method for solid-phase microextraction. The device comprises a syringe with a fiber. The syringe comprises a barrel in which a plunger is movably arranged. The plunger comprises an actuating element at one end of the barrel. A needle is arranged at the other end of the barrel. The fiber moves in the longitudinal direction, when the plunger is actuated, and is contained partially in a metal housing, which surrounds the fiber. The metal housing serves as a guard for the fiber.

EP 0 794 822 B1 (Varian) relates to solid-phase microextraction with vibration. An SPME syringe comprises a needle with a fiber, and a piston with a plunger. One end of the fiber comprises means which ensure that the fiber is movable in. the longitudinal direction with the plunger in the piston. These means can be in the form of a drop of epoxy on the fiber. The fiber is partially enclosed by a protective sheath. After a sample has been collected, the plunger is moved back, as a result of which the fiber inside the protective sheath is guided back into the needle. The fiber is secured inside the syringe and moves together with the piston inside the barrel. The hollow needle is connected to the barrel and contains the fiber. The fiber extends beyond the free end of the needle when the piston is depressed inside the barrel. The fiber is located inside the needle when the piston is pulled out relative to the barrel.

WO 2007/032039 A2 (Degli) relates to an automatic SPME device, in particular for a gas chromatograph. The device comprises a hollow needle in which a fiber is guided. One end of the fiber is secured on a plunger via a plastic connector. The device is secured on a Cartesian-guided robotic head.

The known devices for solid-phase microextraction have the disadvantage, however, that they take up quite a large amount of space. Since the fiber is typically fragile, there is also often the danger of the fiber being damaged during the method, for example before, during or after the analysis.

DISCLOSURE OF THE INVENTION

The object of the invention is to create a solid-phase microextraction device which belongs to the technical field mentioned in the introduction and which takes up a small amount of space and is robust.

In the method according to the invention for performing a solid-phase microextraction, a holding device connected to an extraction device and secured on an adapter is held, while an actuating device connected to a guide device is moved.

During the solid-phase microextraction (hereinafter SPME), the extraction device is therefore preferably held stationary with respect to the adapter. This has the advantage that the position of the extraction device can be determined unambiguously by the position of the adapter. While the guide device is actuated, the extraction device can be held stationary in the matrix. It is thus possible to prevent a situation where the extraction device touches the container and the measurement result is thus rendered incorrect or the extraction device is even damaged. This advantage is of particular benefit in the case of a manually actuated device.

In a preferred embodiment, the adapter can be secured on a robotic arm, in particular on a robotic arm of an automatic analysis appliance. By a movement of the adapter, for example by means of a robotic arm, superimposed movements can be executed, such that it is possible to simulate holding the actuating device stationary and at the same time moving the holding device. For this purpose, for example, the adapter can be moved in one direction, while the actuating device is moved in the opposite direction.

A device for performing a solid-phase microextraction comprises an actuating device connected to a guide device, and a holding device connected to an extraction device, wherein the extraction device is guided at least partially in the guide device, and wherein the extraction device is movable relative to the guide device by means of an actuation of the actuating device.

The actuating device is connected to the guide device. Thus, during use, the guide device can be actuated while the holding device and the extraction device remain stationary. The extraction device is guided partially inside the guide device and is thus also protected by the guide device. By actuation of the actuating device, the extraction device can be moved, preferably linearly, relative to the guide device.

The connection between the actuating device and the guide device, and between the holding device and the extraction device, can be rigid or releasable. A releasable connection between these elements can be advantageous since, in the event of defects or wear, individual parts can then be replaced, as a result of which maintenance becomes more cost effective.

The actuating device is preferably transferred from a first position, in which the extraction device does not protrude beyond a distal end of the guide device, to a second position, in which the extraction device protrudes at least partially beyond a distal end of the guide device.

This procedure has the advantage that the extraction device can be protected by the guide device during transport. The transport is typically between a sample to be analyzed and an analysis appliance. During the extraction with the extraction device, the extraction device typically protrudes beyond the guide device, that is to say the actuating device is in the second position.

After the analyte to be tested has been extracted from the matrix, the actuating device is preferably transferred from the second position to the first position, such that the extraction device no longer protrudes beyond the distal end of the guide device. In this state, the extraction device lying protected in the guide device can be transported to an analysis appliance. By virtue of the fact that the extraction device does not protrude beyond the guide device during transport, it is possible to prevent further substances from being taken up by the extraction device or to prevent extracted substances from being released by the extraction device. Finally, it is thus possible to substantially avoid falsification of analysis results.

The transfer from the first position to the second position preferably takes place by an actuation of the actuating device, which is connected to the guide device.

The actuation of this device thus preferably takes place in a reverse manner compared to a conventional SPME syringe device, in which an extraction device (fiber) is typically actuated via an actuating element.

The actuating device preferably comprises an actuating element and the holding device comprises a holding element, wherein the actuating element is arranged proximally to the holding element in a longitudinal direction of the device.

The device thus preferably comprises a holding element and an actuating element arranged proximally with respect to the latter, such that the device can in principle be actuated like a conventional syringe. By contrast, however, the actuation of the actuating element does not move a piston but instead the actuating device, which is in turn connected to the guide device. At the same time, the device is held on the holding element, such that, upon actuation of the actuating element, the holding device, connected to the holding element, and therefore also the extraction device are held. The syringe-like structure affords the possibility of designing the device for existing automatic analysis appliances that are designed for syringes. This device can thus be designed as a replacement module for a syringe.

It is clear, however, to a person skilled in the art that the actuating element does not necessarily have to be arranged proximally with respect to the holding element. For example, the actuating device can also be connected to an actuating element which is arranged laterally or otherwise with respect to the actuating device.

The holding device is preferably guided on the actuating element. This permits particularly simple guiding of the holding device relative to the actuating element.

In variants, the actuating element can also be arranged in such a way that no contact with the holding device takes place.

Preferably, the guide device is designed as a needle and the extraction device is designed as a fiber, and the actuating device preferably comprises a barrel in which the holding device is movable in the longitudinal direction. During operation, therefore, the barrel and the needle connected to the barrel are moved.

The actuating device does not necessarily have to be present as a barrel. It may suffice if the actuating device comprises guide elements through which the holding device can be guided in the longitudinal direction. This guide can be configured, for example, as a dovetail guide. Other variations are also known to a person skilled in the art.

The barrel is preferably connected to the actuating element via a securing element, wherein the securing element is arranged in particular in a proximal area of the barrel, on an inner face of the barrel, and preferably protrudes radially inward. The actuating element can thus be connected to the actuating device in a particularly compact manner. The actuating element is therefore preferably guided on the holding element and rigidly connected to the barrel.

In variants, the securing element can also be arranged on an outer face of the actuating device or of the barrel. Moreover, the actuating element can also be connected directly to the actuating device or formed in one piece therewith.

The holding device is preferably designed as a plunger with an axially extending slit for the securing element, and with an axial and preferably central bore for the holding device. In this way, the plunger (which is held stationary during operation) can be guided movably in the barrel and on the actuating element, which is connected to the barrel.

In a particularly preferred embodiment, the plunger is guided movably inside the barrel and coaxially with respect to the barrel. The plunger in turn is guided on the actuating element and coaxially with respect to same. For this purpose, the plunger preferably comprises an axial bore, via which the plunger is guided on the actuating element. This ensures that the force effects lie in each case on the same line, such that no bending moment acts on the device during operation.

Moreover, the plunger preferably comprises at least one axial slit, through which the actuating element is connected to the barrel.

In variants, it is also possible to do without the axial bore in the plunger. In this case, for example, the plunger and the actuating element can each be semi-circular in cross section and thus arranged next to each other in the barrel. In particular, the actuating element can in this case also be formed in one piece with the barrel.

The actuating device is preferably transferred from the first position to the second position with a motor drive. This permits a particularly easily controlled transfer from the first position to the second position. The motor drive can comprise an electric motor, for example. The conversion of the rotational movement into a linear movement can be achieved by means of a spindle, toothed rack and the like. The motor is preferably controlled according to the German patent application DE 10 2009 022 314 A1. Other motor drives and motor controls suitable for the present use are known to a person skilled in the art.

The motor actuation of the actuating device preferably takes place from a first position, in which the extraction device does not protrude beyond a distal end of the guide device, to a second position, in which the extraction device protrudes at least partially beyond a distal end of the guide device. In this way, the "exposure" of the extraction device can be controlled by motor.

In variants, the transfer from the first position to the second position can also take place by other means, in particular manually, pneumatically or hydraulically.

Preferably, the actuating device is moved by gravity from a second position, in which the extraction device protrudes at least partially beyond a distal end of the guide device, to a first position, in which the extraction device does not protrude beyond a distal end of the guide device.

The corresponding device is preferably so configured that, when the drive is switched off, the first position, in which the extraction device does not protrude beyond a distal end of the guide device, is automatically adopted under the effect of gravity. This has the advantage that the extraction device can be protected in a currentless state in each case by the guide device.

However, the transfer of the actuating device from the second position to the first position does not necessarily have to take place exclusively under the effect of gravity. The device preferably additionally comprises a motor drive for this movement. In this case, the device can comprise exactly one motor drive for the transfer of the actuating device between the first position and second position (i.e. for the transfer from the first position to the second position and also for the transfer from the second position to the first position).

In variants, it is also possible to dispense with using gravity for the transfer from the second position to the first position.

In a preferred embodiment, the device is mounted on an adapter. An adapter for receiving a device for performing a solid-phase microextraction and for mounting on a tool holder, in particular on a tool holder of an automatic analysis appliance, comprises a securing device for securing the holding device and a coupling device for coupling the adapter to the tool holder.

The adapter, together with the SPME device, forms a tool which can preferably be used for an automatic analysis appliance. The tool as a whole is preferably exchangeable. In other embodiments, the tool can also comprise a syringe for example, such that the analysis appliance can be used in various ways, wherein, preferably both for the SPME device and also for the syringe, a similar adapter is used with the same coupling parts for the tool holder. Preferably, the tool is the tool described in EP 2 261 676 A1, with the difference that instead of a syringe an SPME device is used.

When they are not being used, the individual tools can be temporarily placed in a parking station automatically by the analysis appliance, by the autosampler, in particular by, for example, a Cartesian robotic arm of the aforementioned appliances, or by hand.

During the actuation of the actuating device, the actuating device is preferably movable relative to the holding device, and the holding device is fixed relative to the tool holder. In this way, the extraction device is in particular fixed relative to the tool holder, as a result of which the extraction device is controllable directly by the positioning of the adapter. This simplifies the control of the device.

Preferably, the actuating device can be actuated by motor in both actuating directions. In this way, the movement of the actuating device can be optimally controlled.

The device preferably comprises a control system for the tool, which control system is configured in such a way that, when the device is switched off, in particular before the tool is uncoupled from the tool holder, the actuating device is actuated in an actuation direction from the second position to the first position. The actuating device is preferably driven by motor from the second position, in which the extraction device protrudes at least partially beyond a distal end of the guide device, to the first position, in which the extraction device does not protrude beyond a distal end of the guide device. This design of the device has the advantage that, when the tool is placed in a parking station, a defined end state is reached independently of the starting state, namely the first position in which the extraction device is protected by the guide device and in which the tool as a whole is particularly compact. This has the further advantage that, upon renewed coupling, the coupling parts are clearly positioned such that the coupling procedure can take place trouble-free.

For the actuation, in particular in both directions of movement, a motor drive is preferably provided, such that the actuation can be controlled.

The adapter also preferably comprises a guide for the guide device, or a needle guide, which is movable relative to the holding device. The needle guide is preferably moved parallel to the actuation of the actuating element, but it can also be moved independently of the actuating device of the SPME device. The latter property has the advantage that, when the needle is inserted into a septum, the needle guide can be moved such that the needle guide supports the needle near the septum in this process and thus prevents damage to the needle by bending forces.

In variants, the SPME device itself can comprise the needle guide. On the other hand, however, it is possible to dispense with the needle guide.

In the known tools, the plunger has to be raised in order to protect the fiber by the needle. Modern autosamplers are typically used with different tools, including syringes. Therefore, the tools and the tool holder are typically designed in such a way that, when a tool comprising a syringe is uncoupled, the plunger is driven into the syringe or is in the lower position. The tool, for placement in a parking station, is therefore more compact and requires less space.

If SPME devices are now to be used as a tool for the same autosampler, the problem arises in principle that, in conventional SPME devices, the fiber is exposed when the plunger is driven in and, as a consequence of this, a lot of space is needed and, furthermore, the fiber may be contaminated or damaged. Therefore, the guide device or the needle with the syringe body is preferably moved, instead of (as is customary) the plunger with the fiber. Thus, when the actuating element (which is formed by the needle and the syringe body) is driven in, the fiber, which is stationary with respect to the tool holder, can be covered by the needle and protected. That is to say, when the tool with SPME device is uncoupled, the fiber is protected by the needle.

Further advantageous embodiments and combinations of features of the invention will become clear from the following detailed description and from the entirety of the patent claims.

BRIEF DESCRIPTION OF THE DRAWINGS

In the drawings used to explain the illustrative embodiment.

In principle, identical parts in the figures are provided with identical reference signs.

WAYS OF IMPLEMENTING THE INVENTION

Figure 1A:
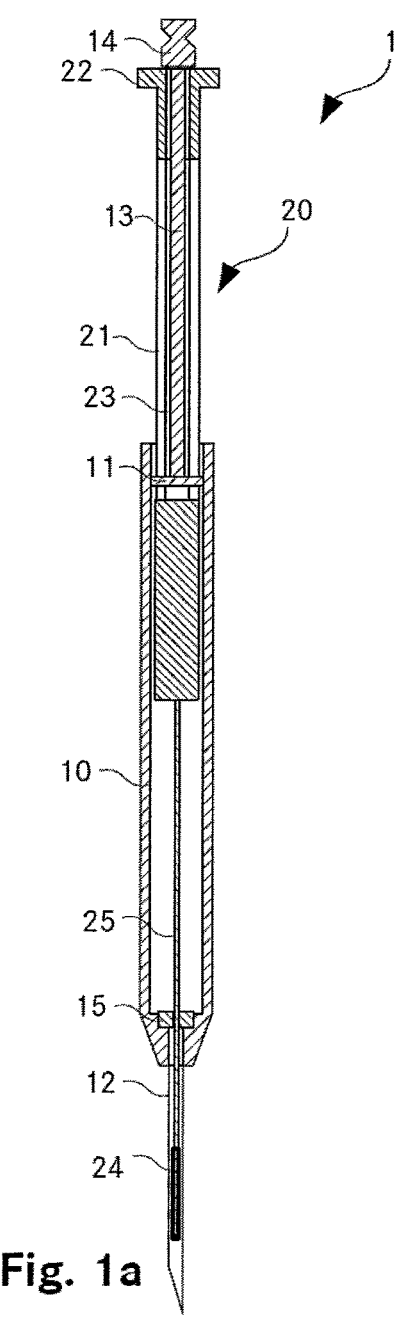
FIG. 1a shows a schematic view of a cross section along a longitudinal axis of a device for performing a solid-phase microextraction, wherein the fiber is covered by the needle.

FIG. 1a shows a schematic view of a cross section along a longitudinal axis of a device 1 for performing a solid-phase microextraction, with a fiber 24 secured on a wire 25, and with a needle 12, a barrel 10 and a plunger 20, wherein the fiber 24 is covered by the needle 12. The device 1 is present in this state during the transport between the extraction and the analysis appliance, and also in the parking station.

The device 1 comprises a plunger 20, of which the basic shape is that of a circular cylinder. In a distal portion of the plunger 20, which portion comprises approximately one third of the length of the plunger 20, the plunger is designed as a completely closed cylinder. In this portion, the plunger 20 is connected to the wire 25, which comprises the fiber 24 at the distal end.

In a middle portion which adjoins the distal portion in the proximal direction, and which comprises approximately half the length of the plunger 20, two slit-like openings 21 are provided which extend in the longitudinal direction and are designed continuously with respect to the plunger 20. The slit-like opening 21 is formed laterally on the plunger as a through-opening. It serves as a recess for a web 11 in the barrel 10 (see below). FIG. 1 shows the cross section through this slit-like opening 21, with no hatching in this area.

The middle area of the plunger 20 is adjoined in the proximal direction by an end area, which comprises approximately one sixth of the length of the plunger 20. This end area is once again designed as a closed hollow cylinder and comprises, at the proximal end, a radially outwardly protruding flange 22, which serves as a holding element in the tool 100 (see below with reference to FIG. 2a).

From the middle area to the proximal area, the plunger 20 has a continuous axial and central bore 23, which opens out in the proximal area of the plunger 20, that is to say in the flange 22.

The barrel 10 has the shape of a hollow circular cylinder which, at the distal end, is tapered via a shoulder. In this area, the barrel 10 comprises a seal 15 in which the wire 25 is guided. The seal 15 permits gas-tight closure of the needle. The internal diameter of the barrel 10 is dimensioned such that the plunger is guided and movable therein in a manner substantially free of play. The needle 12 is secured on the tapered part at the distal end. In a proximal area of the barrel 10, the latter comprises a web 11 which is oriented, at right angles to a longitudinal direction, centrally inside the barrel 10. The web 11 is shaped like a pin. Moreover, the barrel 10 comprises a rod-shaped actuating element 13, which is connected at one end to the web 11 and protrudes beyond the proximal end of the barrel 10. At the proximal end of the actuating element 13, a coupling part 14 is arranged which has a circular cylindrical shape with a circumferential notch. The actuating element 13 serves to actuate, i.e. to move, the actuating device designed as the barrel 10.

Figure 1B:
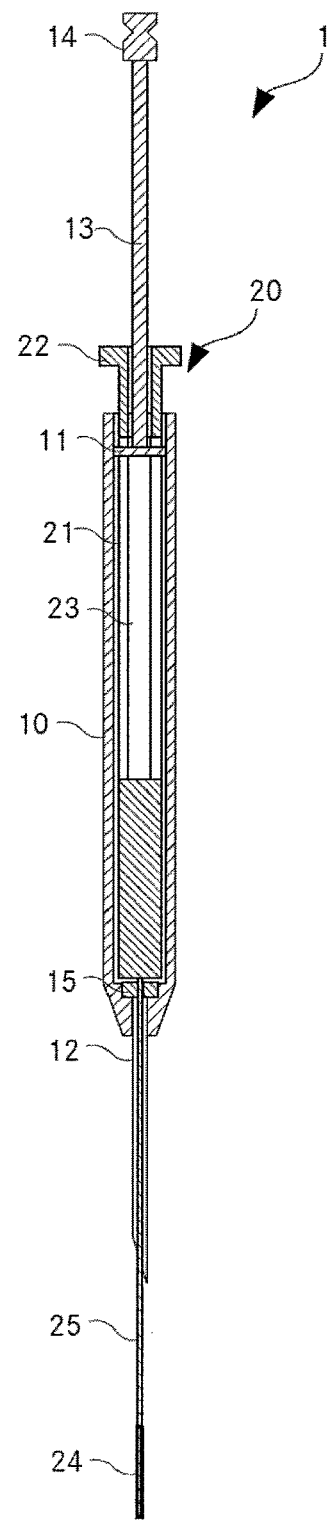
FIG. 1b shows a schematic view according to FIG. 1a, with the fiber not covered.

FIG. 1b shows a schematic view of a cross section along a longitudinal axis of a device 1 for performing a solid-phase microextraction basically according to FIG. 1a, but the actuating device, that is to say the barrel 10, has been moved in the proximal direction over the actuating element 13, such that a distal area of the fiber 24 is exposed. The transition from the state according to FIG. 1a to the state according to FIG. 1b is in fact obtained by pulling the barrel 10 back in the proximal direction by means of the coupling part 14, while the plunger 20 is held stationary. This is effected by a motorized drive of the analysis appliance or of the autosampler on which the tool is coupled.

The device 1 is present in this state typically during the extraction of the analyte from the matrix (e.g. in a vial) or in the analysis appliance during the vaporization or dissolving of the analyte received in the fiber 24 in a gas or liquid chromatograph (GC, HPLC, LC or the like). Before the device 1 in this state is transferred to a parking station, the barrel 10, together with the actuating element 13 and the coupling part 14 and the needle 12, is moved downward by motor, such that the fiber 24 is protected by the needle 12 and such that the device 1 takes up the least possible space in the parking station.

Figures 2A, 2B:
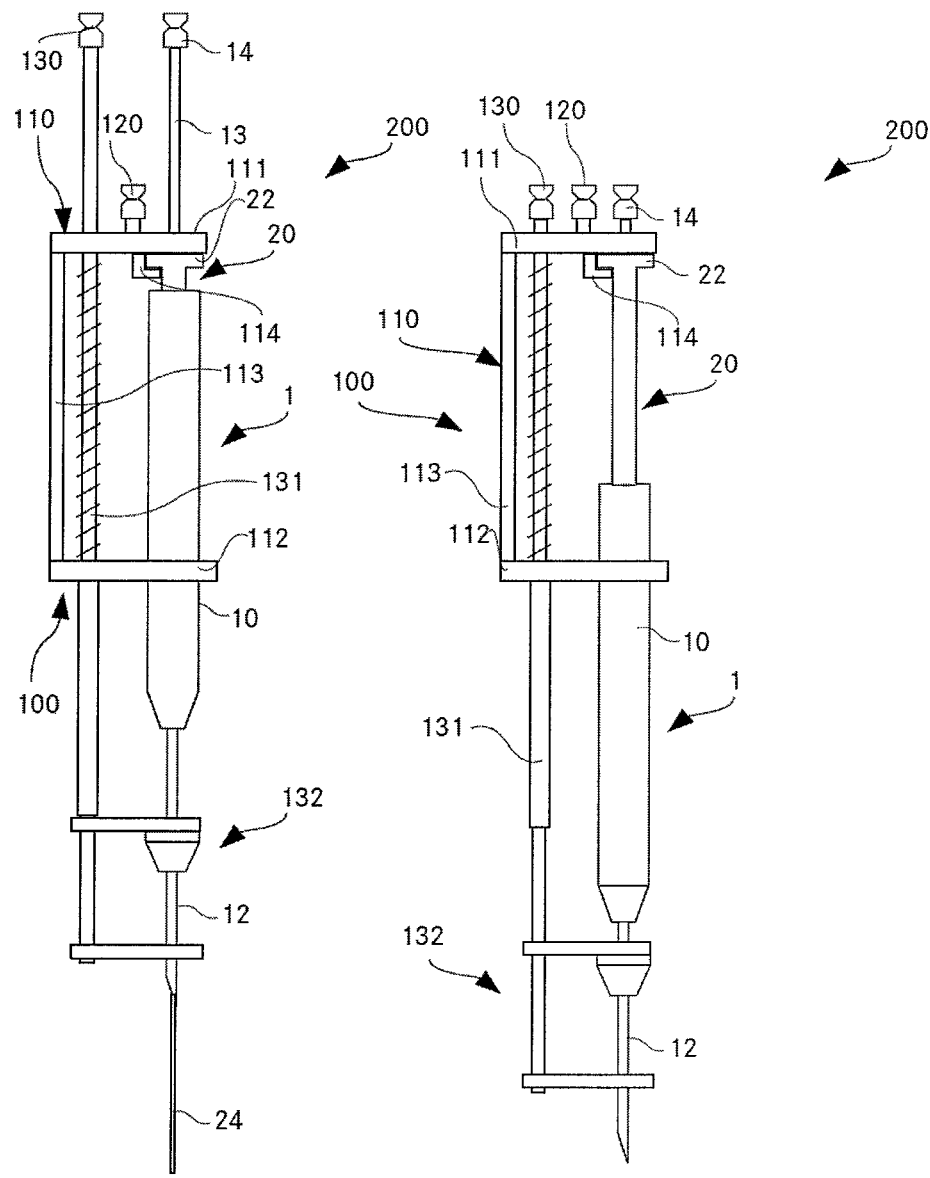
FIG. 2a shows a schematic view of a tool comprising a device for performing a solid-phase micro-extraction and an adapter, wherein the fiber is not covered.
FIG. 2b shows a schematic view of a tool according to FIG. 2a, wherein the fiber is covered by the needle.

FIG. 2a shows a schematic view of a tool 200 comprising a device 1 for performing a solid-phase microextraction and an adapter 100, wherein the fiber 24 is not covered but instead exposed. This can also be seen from the fact that the coupling part 14 has been driven upward in the proximal direction.

The adapter 100 comprises a C-shaped holder 110 with a first, upper rail 111 and with a second, lower rail 112, which are oriented parallel to each other and at a distance from each other and are connected to each other via a holding rail 113 arranged at right angles to the two rails. A holding part 114 for holding or for securing the flange 22 of the plunger 20 is mounted on the inner face, in relation to the C shape, of the first rail 111 of the holder 110. In order to provide a better overall view, this holding part 114 is only indicated schematically. Moreover, the first rail 111 comprises an opening in which the actuating element 13 is movably guided. Lying opposite this, the second rail 112 comprises an opening in which the barrel 10 is movably guided.

The adapter 100 further comprises a coupling part 120, which is designed with the same shape as the coupling part 14 of the actuating element 13. The coupling part 120 serves for coupling to an analysis appliance or to a robotic arm of an analysis appliance (not shown) and is rigidly connected to the holder 110. The tool 200 as a whole is moved via this coupling part 120.

On the holder 110, finally, a coupling part 130 is guided movably in the longitudinal direction and is connected by a bar 131 which is guided through mutually opposite openings in the first and second rails. At the distal end of the bar 131, the latter is connected to a needle guide 132. The coupling part 130 is likewise coupled to the analysis appliance or autosampler, or to the robotic arm. The needle guide 132 can be actuated via the coupling part 130 independently of the actuation of the actuating element 13 and can thus be controlled in such a way that the needle guide 132 follows along for example in parallel with the actuation of the actuating element 13 and therefore of the barrel 10 and of the needle 12. However, since the needle guide 132 can be controlled independently, it can be driven down close to the distal end of the needle 12, for example before the needle 12 is inserted into a septum, in such a way that the needle 12 is optimally supported during the insertion but at the same time can also be pulled back (by the robotic arm) in order to prevent a collision with the septum or with the vial.

FIG. 2b finally shows a schematic view of a tool 200 according to FIG. 2a, wherein the fiber 24 is covered by the needle 12. Both the coupling part 14 and also the coupling part 130 have been moved downward in the distal direction.

As has already been explained with reference to FIGS. 1a and 1b, the movement of the coupling part 14 in the distal direction has the effect that the barrel 10 with the needle 12 is driven downward, such that the needle 12 covers the fiber 24, which is therefore no longer visible in FIG. 2b. At the same time, the needle guide 132 is also driven downward via the coupling part 130.

Before the tool 200 is placed in a parking station, and proceeding from the state shown in FIG. 2a (that is to say with the fiber 24 exposed), the barrel 10 is moved downward by motor, such that the needle 12 slides over the fiber 24 in order to protect the latter when it is not in use. It will also be seen, by comparing with FIG. 2a, that the tool 200 or the device 1 takes up less space in this state. Finally, the coupling parts 14, 120 and 130 are in a clearly defined setting, and therefore the positioning for renewed coupling can be obtained particularly easily.

In a preferred embodiment, the needle guide 132 can also be lowered by motor, such that both the coupling part 14 and also the coupling part 130 moves downward in the parking station.

In the present illustrative embodiment, the actuating device is designed as a barrel 10, the guide device as a needle 12, the holding device as a plunger 20, the extraction device as a fiber 24, and the holding element as a flange 22. However, it is obvious to a person skilled in the art that the individual elements are not to be limited geometrically to the described illustrative embodiment and that they can also be modified in any desired manner without departing from the underlying concept of the invention.

The plunger 20 can also be designed without an axial bore 23. In this case, the coupling part 14 can be secured via an axial rail mounted eccentrically on the barrel 10, such that the actuating element 13 and the plunger 20 are not oriented coaxially.

The plunger 20 is preferably made in one piece, for example from a plastic, although it can also be composed of several parts. Moreover, the plunger 20 can also be composed of two halves, for example produced by injection molding, which are then welded together. The individual parts of the device are preferably made of plastic, although they can also comprise parts made of metal, metal alloys or composite materials. In particular, the needle 12 is preferably made of metal. Instead of the wire 25, it is also possible to provide an inner needle which is made in particular of metal and in which the fiber or a coated fiber is guided. The fiber is preferably arranged to be fixed in relation to the inner needle and can in particular be connected thereto. The inner needle in this case serves as a guard, in particular as a guard against kinking of the fiber.

It may be stated in conclusion that, with the method according to the invention and with the SPME device, a particularly compact and versatile tool is created.

The invention claimed is:

1. An arrangement for performing a solid-phase micro-extraction, comprising:
   an apparatus including an actuating device connected to a guide device;
   a holding device connected to an extraction device, wherein the extraction device is guided at least partially in the guide device; and
   an adapter receiving the apparatus and mounting the apparatus on a tool holder, the adapter fixedly securing the holding device to the tool holder and the extraction device is stationary with respect to the adapter,
   wherein said guide device is movable relative to said extraction device by means of an actuation of the actuating device.

2. The arrangement according to claim 1, wherein the actuating device comprises an actuating element and the holding device comprises a holding element, and said actuating element is arranged proximally to the holding element in a longitudinal direction of relative movement.

3. The arrangement according to claim 2, wherein the holding device guides the relative movement of the actuating element.

4. The arrangement according to claim 1, wherein the guide device is a needle and the extraction device is a fiber, and the actuating device comprises a barrel in which the holding device is movable in the longitudinal direction.

5. The arrangement according to claim 4, wherein the barrel is connected to the actuating element by a securing element arranged on an inner face of the barrel.

6. The arrangement according to claim 5, wherein the holding device is a plunger having an axially extending slit for the securing element and an axial bore for the actuating element.

7. The arrangement according to claim 1, further comprising a motor for moving the actuating device in an actuation direction.

8. The arrangement according to claim 5, wherein the securing element is arranged in a proximal area of the barrel.

9. The arrangement according to claim 5, wherein the securing element protrudes radially inward.

10. An automatic analysis appliance comprising:
    an apparatus according to claim 1; and
    a device for performing a solid-phase micro-extraction.

11. Apparatus for performing a solid-phase micro-extraction, comprising
    an actuating device connected to a needle,
    a holding device connected to a fiber, wherein the fiber is guided at least partially in the needle,
    an adapter receiving the apparatus and mounting the apparatus on a tool holder, the adapter fixedly securing the holding device to the tool holder;
    wherein said needle is movable relative to said fiber by means of an actuation of the actuating device.

* * * * *